United States Patent

Lucast et al.

[11] Patent Number: 6,103,369
[45] Date of Patent: *Aug. 15, 2000

[54] MULTI-LAYERED DRESSING

[75] Inventors: Donald H. Lucast; Steven B. Heinecke, both of St. Paul, Minn.

[73] Assignee: 3M Innovative Properties Company

[*] Notice: This patent issued on a continued prosecution application filed under 37 CFR 1.53(d), and is subject to the twenty year patent term provisions of 35 U.S.C. 154(a)(2).

[21] Appl. No.: 07/887,534

[22] Filed: May 21, 1992

Related U.S. Application Data

[63] Continuation of application No. 07/458,910, Dec. 29, 1989, abandoned.

[51] Int. Cl.[7] .............................. A61F 13/02; B32B 7/12
[52] U.S. Cl. .............................. 428/354; 602/54; 602/55; 602/903
[58] Field of Search .............................. 602/54, 55, 903; 428/354

[56] References Cited

U.S. PATENT DOCUMENTS

| | | | |
|---|---|---|---|
| Re. 31,887 | 5/1985 | Hodgson | 428/355 |
| 3,663,351 | 5/1972 | Murphy | 161/159 |
| 3,800,792 | 4/1974 | McKnight et al. | 128/156 |
| 3,849,238 | 11/1974 | Gould et al. | 161/159 |
| 4,112,177 | 9/1978 | Salditt et al. | 428/304 |
| 4,260,659 | 4/1981 | Gubran | 428/217 |
| 4,263,360 | 4/1981 | Adelman | 428/238 |
| 4,499,896 | 2/1985 | Heinecke | 128/156 |
| 4,538,603 | 9/1985 | Pawelchak et al. | 128/156 |
| 4,559,938 | 12/1985 | Metcalfe | 128/156 |
| 4,595,001 | 6/1986 | Potter et al. | 128/156 |
| 4,598,004 | 7/1986 | Heinecke | 428/40 |
| 4,631,227 | 12/1986 | Nakamura | 128/156 X |
| 4,773,408 | 9/1988 | Cilento et al. | 602/55 X |
| 4,773,409 | 9/1988 | Cilento et al. | 128/156 |
| 4,784,653 | 11/1988 | Bolton et al. | 602/54 |
| 4,798,201 | 1/1989 | Rawlings et al. | 128/156 |
| 4,818,600 | 4/1989 | Braun et al. | 428/290 |
| 4,832,009 | 5/1989 | Dillon | 128/156 |
| 4,909,244 | 3/1990 | Quarfoot et al. | 128/156 |
| 4,995,382 | 2/1991 | Lang et al. | 602/55 |
| 5,025,783 | 6/1991 | Lamb | 602/54 |
| 5,153,040 | 10/1992 | Faasse, Jr. | 602/54 X |

FOREIGN PATENT DOCUMENTS

| | | |
|---|---|---|
| 0 257 133 | 3/1988 | European Pat. Off. |
| 0304536 | 3/1989 | European Pat. Off. |
| 0327328 | 8/1989 | European Pat. Off. |
| 0368541 | 5/1990 | European Pat. Off. |
| WO-A-8901345 | 2/1989 | WIPO |

*Primary Examiner*—Daniel Zirker
*Attorney, Agent, or Firm*—Gary L. Griswold; Robert W. Sprague; Dale A. Bjorkman

[57] ABSTRACT

A highly moisture vapor transmissive adhesive composite is disclosed comprising at least three layers, a polymeric backing layer, a high moisture vapor transmission layer, and a skin contacting adhesive layer. The high moisture vapor transmission layer may be made from a polymeric backing material, an adhesive material or both.

11 Claims, 2 Drawing Sheets

MULTI-LAYERED DRESSING

This is a continuation of application Ser. No. 07/458,910 filed Dec. 29, 1989, abandoned.

FIELD OF THE INVENTION

This invention relates to an adhesive composite for use where high moisture vapor transmission is desirable. This invention particularly relates to an adhesive composite for use as a medical dressing.

BACKGROUND

U.S. Pat. No. 4,112,177 to Salditt et al. discloses a microporous medical pressure-sensitive adhesive tape construction providing a plurality of layers of pressure-sensitive adhesive wherein the total adhesive mass is microporous. As disclosed at column 4, lines 5–9, the firm underlying layer preserves the porous nature of the adhesive mass and the "quickstick" softer outer layer of adhesive adheres very readily to the skin.

U.S. Pat. No. 4,499,896 to Heinecke discloses a wound dressing for wounds having a significant amount of exudate comprising a conformable, moisture vapor permeable, liquid water-impermeable first layer containing at least one hole therein through which exudate can pass, and an imperforate, conformable, liquid water-impermeable, moisture vapor-permeable second layer attached to the first layer and overlaying the hole or holes in the first layer. These layers form a reservoir into which the wound exudate can pass and from which the exudate can evaporate.

European Patent No. 0 257 133 to Ewell discloses a wound dressing containing a fabric layer within which is deposited a layer of a hydrophilic material. Pressure-sensitive adhesive is applied to both faces of the fabric layer. One of the pressure-sensitive adhesive layers is for adhering the dressing onto the patient. A cover layer may be additionally applied to the other pressure-sensitive adhesive layer. The layer of hydrophilic material disposed within the fabric layer is provided to absorb excess exudate from the wound.

U.S. Pat. No. 4,773,409 to Cilento et al. discloses an occlusive wound dressing which includes a flexible closed cell polyurethane foam layer having a pressure-sensitive microporous adhesive applied onto one surface of the foam. A polymeric film may be laminated to the opposite surface of the foam to protect the dressing. The foam itself contains water dispersible, water swellable and/or water absorbing agents.

U.S. Pat. No. 3,800,792 to McKnight et al. discloses a surgical dressing for treatment, particularly of burn wounds, comprising a thick layer of collagen compressed foam film which has been laminated to a thin continuous layer of an inert polymer material such as polyurethane.

U.S. Pat. No. 3,849,238 to Gould et al. discloses an artificial skin comprising a water containing hydrophilic polymer sponge layer and a thinner non-hydrophilic polymer layer which is moisture vapor permeable and gas permeable.

Wound dressings, such as foam and pouch dressings described above, that act as a reservoir for excess exudate perform a specific role in wound therapy, but are not appropriate for all wounds. These wound dressings can be disadvantageous when applied to moderately exudating wounds because, due to their capability of containing fluids, a need for changing these dressings may not be perceived by the user. Because all exudate will be contained by these dressings, they can provide an excessively wet environment for the wound which promotes the growth of bacteria. A reservoir type dressing has a limited useful lifetime on a wound because it eventually will become saturated and must be changed.

As a general rule, as the moisture vapor transmission properties of a film backing or an adhesive are improved, a sacrifice is made in another property. In the case of film backings, an increase in moisture vapor transmission will generally result in a backing with reduced tensile strength and elongation properties. A higher moisture vapor transmissive backing is also typically very sensitive to direct contact with aqueous fluids, which will result in unacceptable swelling of the film so that it no longer stays in place on the substrate. The film may also experience a dramatic loss in tensile strength when exposed to direct aqueous fluid contact.

Similarly, a highly moisture vapor transmissive adhesive will typically display shortcomings in properties such as internal cohesion, which results in residue being left on the skin after removal of the bandage, and an undesirably low level of initial and final adhesion to skin levels.

Transparent dressings currently available on the market utilizing Hytrel™ or Estane™ backings do a generally good job of protecting wounds while permitting some moisture vapor to escape from the site, but could be substantially improved with an increase in moisture vapor transmission if other strength, swell and adhesive properties were not sacrificed.

SUMMARY OF THE INVENTION

The present invention provides an adhesive composite having very high moisture vapor transmission properties with no sacrifice of other desirable properties of a wound dressing. This achievement is accomplished by providing a dressing with one or more backing or adhesive layers having the desired moisture vapor transmission properties and additionally providing a supplemental layer of a corresponding backing or adhesive in a thinner thickness than would be required alone, resulting in a dressing having the desired overall properties of a wound dressing.

Specifically, an adhesive composite is provided comprising a polymeric backing layer, a high moisture transmission layer, and a skin contacting adhesive layer. The high moisture transmission layer exhibits certain minimum moisture vapor transmission properties and is selected from a polymeric backing material and an adhesive material, or a combination thereof. When the high moisture vapor transmission layer is a polymeric backing material, the material has a moisture vapor transmission of at least about 2000 g/m$^2$/24 hrs/37° C./100–20% RH when one mil thick as tested using the Upright Cup method described in detail herein. When the high moisture transmission layer is a polymeric backing material, the polymeric backing layer has a tensile strength when wet that is no more than 30% less than the tensile strength of the backing when dry. When the high moisture transmission layer is an adhesive material, this material is selected from adhesives having a Standardized Transmission Rate as defined herein of at least about 900 g/m$^2$/24 hrs/37° C./100–20% RH. In either case, the material of the polymeric backing layer or the skin contacting adhesive layer is not the same as the material of the high moisture vapor transmission layer. The overall adhesive composite exhibits a moisture vapor transmission rate of at least about 1200 g/m$^2$/24 hrs/37° C./100–20% RH. Preferably the overall adhesive composite exhibits a moisture vapor transmission rate greater than about 1500 g/m$^2$/24 hrs/37° C./100–20% RH, more preferably greater than about 2000 g/m$^2$/24 hrs/37° C./100–20% RH and most preferably greater than about 2500 g/m$^2$/24 hrs/37° C./100–20% RH.

The skin contacting adhesive layer is selected from an adhesive material having an initial adhesion to skin peel strength of at least about 15 g/inch (5.9 g/cm).

It is thus envisioned that the adhesive composite structure will comprise at least three layers. Additional layers may be added as desired. For example, when the high moisture transmission layer is a backing material, it may be desirable to "sandwich" this layer between two polymeric backing layers to protect this layer from contact with liquid moisture.

It has surprisingly been discovered that the disclosed adhesive composite structure exhibits a surprisingly high moisture vapor transmission rate, while at the same time affording excellent strength, swell and adhesive properties.

DESCRIPTION OF THE PREFERRED EMBODIMENTS

Figure 1:
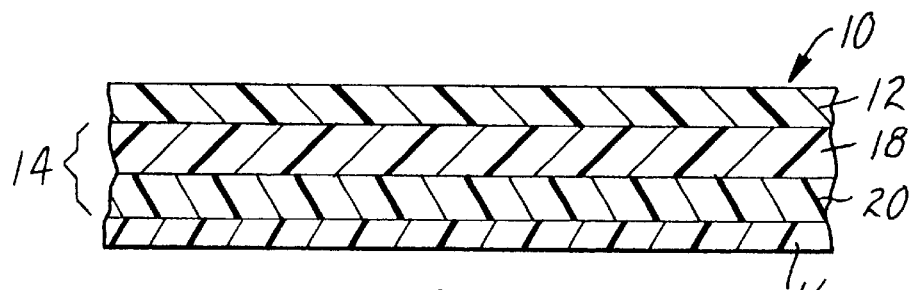
FIG. 1 shows an edge view of a dressing wherein the high moisture transmission layer comprises both an adhesive layer and a backing layer.

Referring now to the drawing, FIG. 1 shows an edge view of dressing 10 having polymeric backing layer 12, high moisture transmission layer 14 and skin contacting adhesive layer 16. Polymeric backing layer 12 is made of a thin polymeric film that is moisture vapor permeable and has a tensile strength when wet that is no more than 30% less than the tensile strength of the backing when dry. Preferably, the wet tensile strength is no more than 20% less than the dry tensile strength and is most preferably no more than 30% less than the dry tensile strength. Wet tensile strength is tested on a one mil thick sample after the entire film sample has been immersed in distilled water for 3 minutes at 37° C. Preferably, this material is liquid and bacteria impermeable. Polymers that satisfy these performance requirements may be prepared from materials such as polyester, polyurethane, polyester block amide or porous polyethylene resins; all having low content of hydrophilic components. Examples of such films are prepared from Estane™ 58309NAT022 (hereafter Estane™ 58309) polyurethane (B. F. Goodrich, Cleveland, Ohio) Rucothane™ polyurethane, Hytrel™ 4056 elastomeric polyester (DuPont, Wilmington, Del.), and Pebax™ 2533 or 3533 polyether block amide (Atochem, Paris, France, distributed in the U.S. by Rilsan Corporation, Glen Rock, N.J.) resins. Polymeric backing layer 12 is a dimensionally stable film, and thus can be relatively thin. Thicknesses of less than about 0.025 mm, and preferably less than about 0.020 mm are envisioned, and are most preferably as thin as possible without introducing pinholes in the material.

High moisture transmission layer 14 comprises high moisture vapor transmission backing layer 18 and high moisture vapor transmission adhesive layer 20. High moisture vapor transmission backing layer 18 is made of a polymeric film backing material that has a moisture vapor transmission rate of at least 2000 g/m$^2$/24 hrs/37° C./100–20% RH when one mil thick as tested using the Upright Cup method (defined herein) and is preferably aqueous fluid and bacteria impermeable. Preferably, the high moisture vapor transmission backing is selected from a material that has a moisture vapor transmission rate that is greater than 2500 g/m$^2$/24 hrs/37° C./100–20% RH, and more preferably greater than 3000 g/m$^2$/24 hrs/37° C./100–20% RH. Examples of materials that will satisfy this requirement include materials containing a relatively high content of hydrophilic components including certain polyether block amides such as Pebax™ 4011RN00 (hereafter Pebax™ 4011) film or porous polyethylenes as described in U.S. Pat. No. 4,539,256. High moisture vapor transmission adhesive layer 20 is an adhesive that has a Standardized Transmission Rate (defined herein) of at least about 900 g/m$^2$/24 hrs/37° C./100–20% RH. Preferred adhesives for use in this layer possess a Standardized Transmission Rate of greater than about 1100 g/m$^2$/24 hrs/37° C./100–20% RH and most preferably greater than about 1400 g/m$^2$/24 hrs/37° C./100–20% RH. These extremely high moisture vapor transmission rates are typically achieved by introducing a hydrophilic element in the adhesive as a comonomer or in a polymeric mixture. An example of such an adhesive formulation would contain iso-octyl acrylate, butyl acrylate, N-vinyl pyrrolidone and methoxy polyethylene oxide acrylate. The inclusion of hydrophilic monomers as alternatives to the N-vinyl pyrrolidone discussed above, such as alkoxypolyethylene, oxide acrylates, is envisioned. An additional adhesive that may be used for this moisture vapor transmission adhesive is a gel-adhesive mixture composition comprising a pressure-sensitive adhesive, a hydrocolloid, and a swelling agent. Skin contacting adhesive layer 16 is a pressure-sensitive adhesive exhibiting low irritation to the skin, preferably a hypoallergenic acrylate copolymer adhesive. The skin contacting adhesive is selected so that the overall dressing has initial adhesion to skin values of at least about 15 g/inch (5.9 g/cm) and preferably greater than about 40 g/inch (15.7 g/cm). Initial adhesion to skin is determined by skin panel testing as described herein with removal of the adhesive composite within about five minutes of application to the subject. Final adhesion to skin values for the overall composite are typically between about 50 to 300 g/inch (19.7 to 118.1 g/cm) and preferably between about 80 to 200 g/inch (31.5 to 78.7 g/cm). Final adhesion to skin is also determined by skin panel testing as described herein with removal from the subject after 48 hours. Due to the presence of the moisture vapor transmission adhesive layer 20, skin contacting adhesive layer 16 need not be thick in order to provide the desired adhesion, cohesion and tack properties for an optimal dressing. It is desirable to reduce the thickness of skin contacting adhesive layer 16 as low as possible in order to maximize the moisture vapor transmission rate of the overall dressing. Preferably, skin contacting adhesive layer 16 is between about ⅓ to ½₀th of the thickness of high moisture vapor transmission adhesive 20, and more preferably ⅕ to ⅒th of the thickness. Similarly, polymeric backing layer 12 is preferably between about ⅓ and ½₀th the thickness of high moisture vapor transmission backing layer 18, and more preferably ⅕ to ⅒th the thickness.

Figure 2:
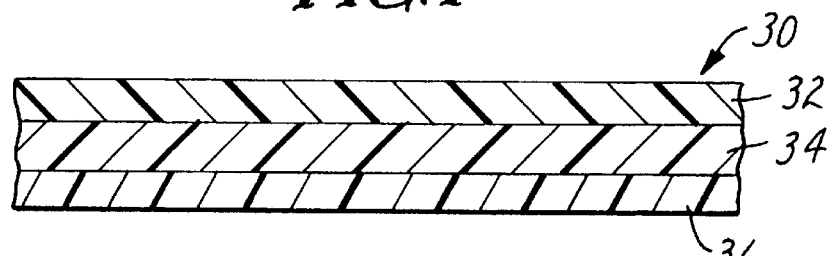
FIG. 2 shows an edge view of a dressing wherein the high moisture transmission layer is a backing layer.

FIG. 2 shows an edge view of dressing 30 comprising polymeric backing layer 32, high moisture vapor transmission backing layer 34 and skin contacting adhesive layer 36. Materials for polymeric backing layer 32 and high moisture vapor transmission backing layer 34 are as described for the corresponding layer as described above for dressing 10. Skin contacting adhesive layer 36 may optionally consist of any adhesive material that provides satisfactory cohesive, adhesive and tack properties. Better adhesion and overall properties of the dressing are generally observed when this adhesive is selected from standard skin contacting adhesives. Because only one adhesive layer is provided, skin contacting adhesive layer 36 should be provided in a standard coating weight for dressings of this type. Thus, skin contacting adhesive layer 36 is typically provided in coating weights of about 1.25 to 5.0 mg/cm$^2$.

Figure 3:
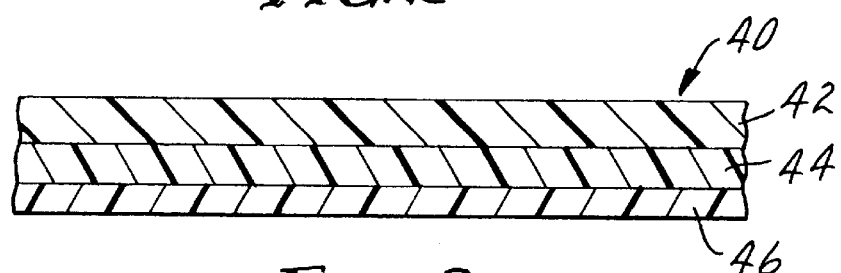
FIG. 3 shows an edge view of a dressing wherein the high moisture transmission layer is an adhesive layer.

FIG. 3 shows an edge view of dressing 40 having polymeric backing layer 42, high moisture vapor transmission adhesive layer 44 and skin contacting adhesive layer 46. Because only one backing layer is provided in dressing 40, backing layer 42 must be of a material and thickness to be acceptable for the intended use of the dressing, and need not be restricted to materials having any specified wet to dry tensile strength ratios. For example, where the dressing is to be used in an environment where water contact from external sources is not expected, the use of highly water absorbent films such as Pebax™ 4011 films is acceptable. Where the backing of the dressing may be exposed to water, as would be expected if it were applied to a hand that would subsequently be washed, a more water resistant backing material such as Estane™ 58309 or Hytrel™ films is desirable. In typical use, a polymeric backing having a wet tensile strength that is no more than 30% less than the tensile strength of the dry backing will generally provide the most satisfactory product. Materials to be used for high moisture vapor transmission adhesive layer 44 and skin contacting adhesive layer 46 may be selected from materials described for the corresponding layers of dressing 10 discussed above.

Figure 4:
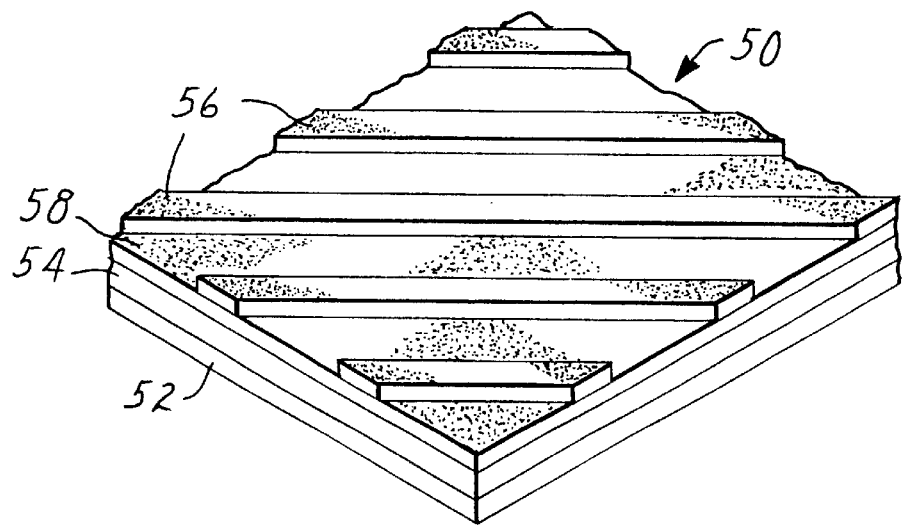
FIG. 4 shows a perspective view of a dressing having a pattern coated adhesive.

FIG. 4 shows a perspective view of dressing 50 comprising polymeric backing layer 52, high moisture vapor transmission backing layer 54, high moisture vapor transmission adhesive layer 58 and pattern coated adhesive 56. Because pattern coated adhesive 56 is not continuous, it allows direct contact of high moisture vapor transmission adhesive layer 58 with the skin or substrate while at the same time taking advantage of the adhesion properties of a regular adhesive. Materials to be used in this embodiment are as indicated for the corresponding layers in the discussion of dressing 10. Dressing 50 provides extremely high moisture vapor transmission rates when high moisture vapor transmission adhesive layer 58 is not exposed to liquid moisture. Thus, this embodiment is particularly useful in applications where the dressing will not be exposed to a large amount of exudate.

Figure 5:
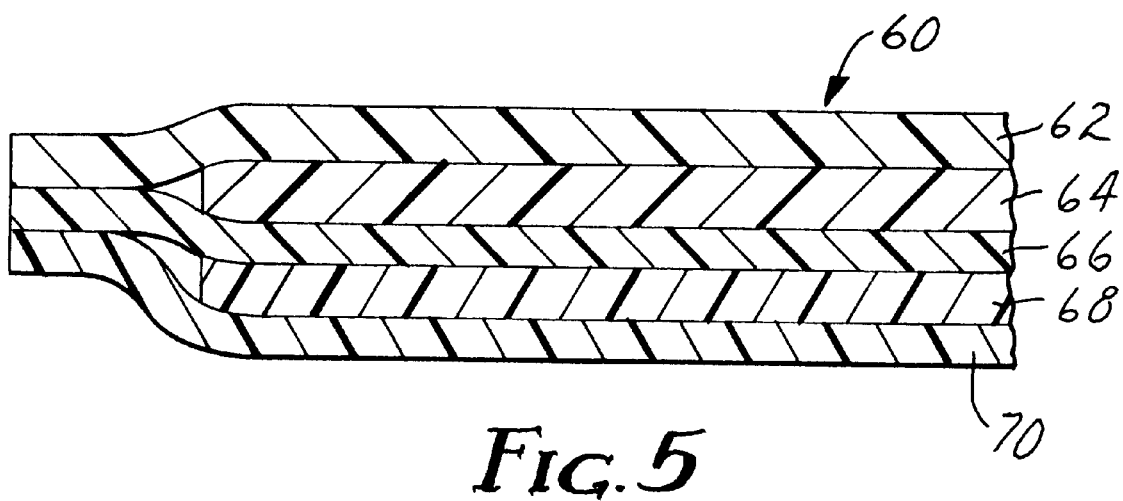
FIG. 5 shows an edge view of a dressing having five layers.

FIG. 5 shows an edge view of dressing 60 which is a "sandwich configuration." Dressing 60 comprises first polymeric backing layer 62, high moisture vapor transmission backing layer 64, second polymeric backing layer 66, high moisture vapor transmission adhesive layer 68 and skin contacting adhesive layer 70. First and second polymeric backing layers 62 and 66 provide particular protection for the high moisture transmission layer 64 from excess swelling due to exposure to liquids. This configuration, therefore, is particularly advantageous for use in wounds having heavy exudate as well as moisture from external sources. As shown, high moisture vapor transmission backing layer 64 and high moisture vapor transmission adhesive layer 68 do not extend to the edge of dressing 60. In this configuration, first polymeric backing layer 62 and second polymeric backing layer 66 contact each other around the entire perimeter of dressing 60, thereby completely enveloping high moisture vapor transmission backing layer 64 in a polymeric backing. Similarly, high moisture vapor transmission adhesive layer 68 is completely enveloped by second polymeric backing layer 66 and skin contacting adhesive layer 70. An alternative configuration where the high moisture vapor transmission layers are not completely enveloped is also envisioned. Such an embodiment would expose the very edges of the high moisture vapor transmission layers to potential contact with liquid, but because the total surface area exposed is very small, these liquid sensitive materials would be for the most part protected from direct liquid contact.

The Standardized Transmission Rate for an adhesive is determined by applying the adhesive at a coating weight of 2.5 mg/cm$^2$ to a specific one mil thick substrate to enable testing of the moisture vapor transmission properties of the adhesive itself. The substrate is a polyurethane film extruded from a resin comprising 1000 molecular weight polytetramethylene oxide (commercially available as PolyMeg™ 1000 from Quaker Oats Chemical, W. Lafayette, Ind.), methylene diisocyanate (commercially available from Mobay Corp., Pittsburgh, Pa.), and 1,4-butanediol (commercially available from Aldrich Chemical Co., Milwaukee, Wis.) in the mole ratio of 1:2:1, respectively. Such a polyurethane resin is commercially available as Estane™ 58309 resin from B. F. Goodrich, Cleveland, Ohio. This substrate polyurethane film has a moisture vapor transmission rate when uncoated of about 1200 g/m$^2$/24 hrs/37° C./100–20% RH when one mil thick using the Upright Cup method as described herein.

As discussed above, the polymeric backing layer is primarily present to provide dimensional stability to the adhesive composite. Thus, while this layer will possess moisture vapor transmissive properties, it will at the same time provide tensile strength to the adhesive composite as well as a measure of conformability, as embodied in elongation and flexion. These properties are provided by polymeric films, such as those disclosed in U.S. Pat. Nos. 3,645,835 and 4,595,001.

Particularly preferred polymeric backing materials are polyurethane and elastomeric polyether films. These films combine the desirable properties of resiliency, high moisture vapor permeability and transparency.

The high moisture transmission layer is a polymeric film, a layer of adhesive or a combination thereof. Preferably, this layer absorbs between 10 and 100% of its own weight in water, and therefore does not absorb or take up significant quantities of water or moisture to act as a reservoir. Rather, it acts as an expediter to encourage the flow of moisture vapor through the composite. Because the high moisture transmission layer, when in an uninterrupted layer, is liquid water impermeable and will suppress bacterial flow, this layer provides additional protective properties to the overall adhesive composite when used as a direct wound dressing.

Because the high moisture transmission layer is not acting as a fluid reservoir, the composite will not have to be replaced due to fluid saturation. The composite additionally presents an extremely low profile due to the thinness of each layer of the composite, thereby avoiding catching of the dressing on clothing or bedding. It is envisioned that the overall profile of the subject dressings preferably will not exceed about 0.5 mm, more preferably about 0.2 mm, and most preferably about 0.05 mm in thickness.

The property of transparency or translucency can be extremely desirable and important for wound dressings to enable inspection of the wound site without removal of the dressing itself. It is difficult to achieve this property while at the same time providing a composite having the requisite strength, swell and moisture vapor transmission properties. By acting as a moisture vapor transmission composite rather than a fluid reservoir and with careful selection of materials, it is possible to make a composite that is transparent or highly translucent.

An alternative high moisture vapor transmission adhesive for use in the present composites is a gel-adhesive composite comprising a pressure sensitive adhesive, a hydrocolloid, and a swelling agent. The pressure sensitive adhesive used in the gel-adhesive composite may be a broad variety of adhesives which may uniformly disperse a gel therein. The adhesive must be dermatologically acceptable and tacky at room temperature as well as at skin temperature of patients. The adhesive may be prepared from any combination of homopolymers, oligomers or blends thereof to produce a polymeric composition containing polyacrylates, polyolefins, silicone adhesives, polyvinyl ethers, polyesters, and polyurethanes.

The hydrocolloid used in the gel-adhesive composite may be a broad variety of swellable compositions of naturally occurring or synthetic compositions which are compatible with the swelling agents, such that the shear modulus of the gel of the swollen hydrocolloid should not be greater than about $6.2 \times 10^6$ dynes/cm$^2$. Hydrocolloids that may be used include selected acrylate polymers having hydroxy or amine functionalities, poly (N-vinyl lactams), polyacrylamides, polysaccharides, natural and synthetically modified alginates, guar gums, natural and synthetically modified celluloses, chitosan, chitin, polyoxyalkylenes, and polyvinyl alcohols.

The swelling agent for the gel-adhesive composite may be a broad variety of non-volatile liquids which are incompatible or immiscible with the pressure sensitive adhesive. Migration or "blooming" of the swelling agent from the gel into the adhesive and to the surface of the composition that would adversely impact the adhesive properties of the composition is minimized by selecting swelling agents that are incompatible with the pressure sensitive adhesive. While optimally no swelling agent should migrate into the adhesive matrix, amounts of swelling agent less than 5 weight percent of the pressure sensitive adhesive may migrate from the dispersed gel into the adhesive matrix without loss of moisture vapor transmission properties by the gel and without loss of adhesion properties by the adhesive matrix. The use of non-volatile swelling agents results in a hydrocolloid that has a longer useful lifetime. Swelling agents that may be used in the gel-adhesive composite include room temperature liquid polyols (including polyhydric alcohols), such as glycerol, propylene glycol, poly(ethylene) glycol (having a molecular weight in the range of about 200 to about 600) and polypropylene glycol (having a molecular weight in the range of about 350 to about 1000); room temperature solid polyols (including polyhydric alcohols) (such as sorbitol, erthyritol, threitol, ribotol, arabinitol, xylitol, allitol, talitol, mannitol, glucitol, glactitol, iditol, pentaerythritol, heptitol, octitol, nonitol, decitol, and dodenitol) blended with a room temperature liquid polyol; monoanhydroalditols (such as styracitol, polyalitol, D-fructose, 1,4 anhydro-D-mannitol and 1,4 anhydro-D-glucitol) blended with a room temperature liquid polyol; monosaccharides (such as pentoses, hexoses and heptoses) blended with a room temperature liquid polyol; and ether alcohols (such as poly(ethylene) glycol ether (having a molecular weight in the range of 600 to 20,000) and polypropylene glycol ether (having a molecular weight in the range of 1,000 to 5,000) blended with a room temperature liquid polyol.

Depending on the properties desired for the gel-adhesive composite, the range of weight fraction ratios for the hydrocolloid to the swelling agent can be from about 3:1 to about 1:99. At the ratio of about 3:1, there is sufficient swelling agent to achieve a soft and pliable gel suitable for providing a high moisture vapor transmission rate to the mixture composition. At the ratio of about 1:99, there is sufficient hydrocolloid to prevent the swelling agent from migrating into the pressure sensitive adhesive and blooming to the surface of the composition.

The gel should be sufficiently soft and pliable to maintain adhesiveness of the pressure sensitive adhesive in moist skin environments and to provide a high moisture vapor transmission rate. Shear modulus is a measurement of the softness and pliability desired for the gel of the present invention. Generally the shear modulus should be less than $6.2 \times 10(6)$ dynes/cm(2). The shear modulus was measured by hydraulically pressing the adhesive samples between release liners to a thickness of 1 mm. The resultant gel films were cut to 50 mm diameter circles and tested between 50 mm diameter parallel plates at 22° C. on a "Rheometrics Mechanical Spectrometer", Model 605 manufactured by Rheometrics Inc., Piscataway, N.J. These details and ASTM D 4065-82 describe the technique used.

The gel-adhesive composite is prepared by first separately preparing the pressure sensitive adhesive and the gel, followed by mixing them to form the composite. The pressure sensitive adhesive may be prepared by solution or bulk polymerization. The hydrocolloid may be prepared by free radical polymerization of the approximate monomers or prepolymers in bulk or in solution followed by grinding of the resultant hydrocolloid polymer into fine particles, which are then swollen by mixing with the swelling agent to form the gel.

The skin contacting adhesive provides the necessary properties to make the composite compatible with contact with the intended substrate, particularly human skin. Particularly, this adhesive will provide the necessary properties of tack, adhesion, cohesion and removability.

The preferred pressure-sensitive adhesives which can be used as the skin contacting adhesive are the normal adhesives which are applied to the skin such as the acrylate copolymers described in U.S. Pat. No. Re. 24,906, particularly a 97:3 iso-octyl acrylate:acrylamide copolymer. Other useful adhesives are those described in U.S. Pat. No. 3,389,827, which discloses block copolymers having three or more polymer block structures having a general configuration —A—B—A— wherein each A block is a thermoplastic polymer with a glass transition temperature above room temperature (i.e., above about 20° C.) having an average molecular weight between about 5000 and 125,000 and the B block is a polymer of a conjugated diene having an average molecular weight between about 15,000 and 250,000. Additional examples of useful adhesives are iso-octyl acrylate/N-vinyl pyrrolidone copolymer adhesives and crosslinked acrylate adhesives such as, for example, those described in U.S. Pat. No. 4,112,213. Inclusion of medicaments or antimicrobial agents such as iodine in the adhesive is useful for wound healing and preventing infection. U.S. Pat. Nos. 4,310,509 and 4,323,557 describe such antimicrobial adhesives.

The dressing of the present invention may be made by conventional techniques (e.g., extrusion, solvent casting, calendering, and laminating and the like) which are familiar to those skilled in the art. (See Modern Plastics Encyclopedia McGraw Hill, 1984–85; Coating and Laminating Machines, Weiss Coverting Technology Co., 1977.)

The dressing as described above is typically provided as individual dressings wherein the adhesive layer is attached to a liner coated with a release material. Because most of the embodiments of the present invention will result in composites that are flimsy and difficult to handle, it is envisioned that one of the many delivery systems known in the art would be utilized to deliver the composite to the intended substrate. Examples of such delivery systems are disclosed in U.S. Pat. Nos. 4,614,183 and 4,598,004.

Alternatively, the dressing may be provided in a roll form.

The dressing of the present invention is further illustrated by the following non-limiting examples.

EXAMPLE 1

A moisture vapor transmission backing having a 1.0 mil (28 micron) thickness was extruded from Pebax 4011 polyether block amide resin using conventional extrusion techniques. A polymeric backing layer was applied to one face of the Pebax film by coating it with a 15% solids solution of Estane 58309 polyurethane resin in tetrahydrofuran using a #20 Meyer bar and drying the coated film at about 95° C. for 10 minutes.

A gel-adhesive composite comprising a base adhesive consisting of a copolymer of iso-octyl acrylate/N-vinyl pyrrolidone copolymer (91/9) and gel particles was prepared as follows: A solution of ethyldine bis(N-vinyl-2-pyrrolidone) (0.16 parts), 2-hydroxy-2-methyl-1-phenyl-1-propanone (1.0 part) and N-vinyl-2-pyrrolidone (100 parts) was placed in a flat dish (1.3 centimeters deep solution) and irradiated through a 0.5 centimeter thick quartz plate with a "Sylvania Sunlamp #052" (from GTE Sylvania, Inc., Manchester, N.H.) for 20 minutes. The lamp was placed approximately 40 centimeters from the quartz plate. The resultant cross-linked poly(N-vinyl pyrrolidone) (PNVP) was ground into a powder (average particle size less than 0.25 centimeters) using a blender and then emulsified in water and reprecipitated in acetone three times to remove residual monomers. The polymer was dried in a vacuum oven at 65° C. and then ground into a fine powder using a Brinkman Retsch Grinder (available from Brinkman Instruments Company, Westbury, N.Y.). The grinder was outfitted with a 750 micro grate and operated at 20,000 rpm to produce a particle size distribution of 750 microns and smaller, with the majority of particles (weight %) between 25 and 200 microns in size. Six parts of the PNVP were mixed with 14 parts of glycerol and 61 parts deionized water and the mixture sheared in a blender to maintain the small particle size of the gels by reducing agglomeration of the particles while forming a swollen gel. A 28% solids solution (w/w) of the (91/9) iso-octyl acrylate/N-vinyl-2-pyrrolidone copolymer base polymer in a 50/50 heptane/ethyl acetate solvent mixture (71.4 parts) was blended with the swollen hydrogel particles (81 parts) and n-heptane (21.4 parts) and the mixture was dispersed with a Laboratory Dispersator, Series 2000 Model 84 (available from Premier Mill Corporation, Reading, Pa.) for several minutes until the gel appeared evenly dispersed. The mixture was allowed to stand for about one minute to expel air bubbles, after which it was coated on the polyethylene-coated side of a release liner. The release liner consisted of a polyethylene coated bleached kraft (83 pounds, 37682 grams), the polyethylene coated side being further treated with a silicone release, (commercially available as Polyslik™ S-8004 from H. P. Smith, Chicago, Ill.) at a coating weight of twenty five grams per square meter utilizing a standard horizontal knife coater. The gel-adhesive composite was dried 60 minutes under ambient conditions and followed by drying at 79° C. for 15 minutes.

An adhesive construction was prepared by laminating the adhesive to the uncoated side of the Pebax™ film without removing the release liner so that it could serve as a polymeric liner for the adhesive construction.

EXAMPLE 2

An adhesive construction was prepared by laminating two layers of adhesive, the high moisture transmission layer comprising 60 parts n-butyl acrylate, 25 parts N-vinyl pyrrolidone and 15 parts ethylene oxide acrylate and the skin contacting layer comprising 70 parts iso-octyl acrylate, 15 parts of ethylene oxide acrylate and 15 parts acrylic acid. The second layer of adhesive was applied over the first adhesive layer, and this laminate applied to the Pebax™ backing of Example 1 with the high moisture transmission layer in direct contact with the Pebax™ backing. Both adhesives were prepared in accordance with U.S. Pat. No. Re. 24,906, which is incorporated herein by reference, and coated on the Pebax™ backing as described in Example 1 at coating weights of twenty g/m² for the first adhesive and ten g/m² for the second adhesive.

EXAMPLE 3

An adhesive construction was prepared by laminating the skin contacting adhesive composition of Example 2 at a weight of twenty g/m² to the Pebax™/Estane™ backing of Example 1.

EXAMPLE 4

An adhesive construction was prepared by laminating a single skin contacting layer of adhesive comprising 70 parts n-butyl acrylate, 20 parts ethylene oxide acrylate and 10 parts acrylic acid prepared according to U.S. Pat. No. Re. 24,906 at a weight of twenty five g/m² to the Pebax™/Estane™ backing of Example 1.

EXAMPLE 5

A backing was prepared as described in Example 1 except that a layer of Estane™ 58309 film was applied to both sides of the Pebax™ backing according to the procedures of Example 1.

An adhesive construction was prepared by laminating a 50 g/m² coating of the adhesive of Example 1 to the above described double coated Pebax™ backing with the skin-contacting adhesive exposed.

EXAMPLE 6

An adhesive construction was prepared by laminating the two-layer adhesive system of Example 2 to a 25 micron backing of Pebax™ 4011 film with skin contacting adhesive exposed.

The composites as shown in the examples above were evaluated for water swell, tensile strength and moisture vapor transmission properties. Test methods used are discussed below, and results are shown in Table I.

SWELL

Test materials were evaluated for dimensional stability when in contact with water using a simple swell test. The length of each sample was initially measured dry and then submersed in a 37° C. distilled water bath for 3 minutes. The samples were then removed and the length was again measured. The linear swell was reported in % increase in length with thickness being neglected.

TENSILE STRENGTH

Tensile strength of the samples was determined in both dry and wet (soaked as described in the swell test) conditions as generally described in ASTM D 882 and ASTM D 3759. Results are recorded in Newtons/100 mm and the % change was recorded for the soaked sample. Tensiles referred to herein were effectively determined using an Intelect II from Thwing Albert Instrument Co., Philadelphia, Pa. using a cross-head speed of 25.4 cm per minute. The gauge length was set at 5 cm with the test sample 2.54 cm in width.

SKIN ADHESION

Skin adhesion was determined by the use of skin panels.

The adhesive-coated sheet material to be tested was cut into 1×3 inch (2.5×7.6 cm) strips which were applied to the (dry) backs of each of 6 individuals (i.e., 3 men and 3 women, randomly selected) who were lying on procedure tables in prone positions with arms at the insides and heads turned to one side. For each individual, each of three strips of the sheet material was applied to one or the other side of the spinal column and was positioned such that the length of the strip was at right angles to the spinal column. The strips were applied without tension or pulling of the skin and there was at least a 32 to 95 mm space between each strip. After all strips were in place, a 2 kg rubber roller (according to the specifications found in the 7th Edition of the Pressure-Sensitive Tape Council Brochure (1976)) was rolled along the length of each strip. When rolling the strip, no manual pressure was applied to the roller.

To determine the adhesive value, each strip was removed at a 90° angle from a line formed by the spinal column using a conventional adhesion tester having a 114 kg test line and a 2.54 cm clip attached to the test line. The clip was attached to the edge of the strip which was farthest from the spinal cord, the clip being attached by manually lifting about 1.27 cm of that edge of the strip and attaching the clip thereto. This orientation permits the strip to be removed starting from the outside of the back towards the spine so that pull is with the direction of fine hair growth on the back. This is facilitated by positioning the adhesion tester opposite the side of the individual's back from which the strip is to be removed. The adhesion tester was aligned with, and was at the same height as, the strip to be removed in order to maintain the 90° removal angle. The strip was pulled over itself in a plane parallel (180°) to the back and the rate of removal was 6 inches (15.2 cm) per minute. To determine initial skin adhesion, the strip was removed within about 5 minutes of its application to the back.

A suitable adhesion tester for use in this Test Method is a conventional motor driven screw with moving carriage and a transducer that is connected to a load cell accessory. Removal force placed on the transducer results in a signal change which is passed through a readout meter to a strip chart recorder.

MOISTURE VAPOR TRANSMISSION RATE

Test materials were evaluated for moisture vapor transmission using water contact (inverted cup) and vapor contact (Upright Cup) methods which were a modified version of the test methods described in ASTM E96.

Inverted Cup

After placing 25 ml of distilled water in a Paddington cup having a 3.5 cm opening (commercially available from Bio-Med Engineering, LTD, Liversedge, West Yorkshire, England), a 2.54 cm diameter sample of the test material was clamped to the flange using sealing rings and screw clamps. The sample was then placed in a circulating oven in an inverted position and was maintained at 37° C. and a relative humidity of 20%. After preconditioning for about 4 hours, an initial sample weight was recorded and the sample returned to the inverted position in the oven. The cup was removed from the oven between 16 and 24 hours later and re-weighed to determine moisture loss. The moisture vapor transmission of each sample was reported in grams per square meter per 24 hours.

Upright Cup 50 mls distilled water was placed in a jar having a 2.54 cm opening. A 3.8 cm diameter sample of the test material was clamped to the flange using sealing rings and screw clamps. The sample was then placed in a circulating oven in an upright position and was maintained at 37° C. and a relative humidity of 20%. After preconditioning for about 4 hours, an initial sample weight was recorded and the sample returned to the upright position in the oven. The cup was removed from the oven between 16 and 24 hours later and re-weighed to determine moisture loss. The moisture vapor transmission of each sample was reported in grams per square meter per 24 hours.

TABLE I

| Example | Description | Tensile N/100 mm width | | | | MVTR $g/m^2/24$ h |
| | | Dry | Wet | % Change | % Swell | Up/Inv |
| --- | --- | --- | --- | --- | --- | --- |
| 1 | IOA/NVP/GEL PEBAX ™/ESTANE ™ | 59.5 | 28.0 | 53 | 8 | 2250/7400 |
| 2 | IOA/EOA/AA IOA/nBA/NVP/EOA PEBAX ™/ESTANE ™ | 141.9 | 108.6 | 23 | | 1150/3450 |
| 3 | IOA/EOA/AA PEBAX ™/ESTANE ™ | | | | | 1600/6100 |
| 4 | nBA/EOA/AA PEBAX ™/ESTANE ™ | 101.6 | 61.3 | 40 | | 2050/3400 |
| 6 | IOA/EOA/AA IOA/nBA/NVP/EOA PEBAX ™ | | | | 37 | 2250/12150 |
| | TEGADERM ™[1] 1626 | 99.8 | 99.8 | 0 | 0 | 650/850 |
| | ESTANE ™ 58309[2] | 78.8 | 84.1 | 6 | 0 | 1550/3300 |
| | PEBAX ™ 4011[2] | 75.3 | 14.0 | 81 | 40 | 4650/>25000 |

TABLE I-continued

| Example | Description | Tensile N/100 mm width | | | | MVTR g/m²/24 h |
| --- | --- | --- | --- | --- | --- | --- |
| | | Dry | Wet | % Change | % Swell | Up/Inv |
| | PEBAX ™/ESTANE ™[3] | 78.8 | 29.8 | 62 | | 2350/10550 |
| | ESTANE ™/PEBAX ™/ESTANE ™[4] | 119.1 | 89.3 | 25 | 4 | |

[1] commercially available from 3M Company, St. Paul, MN
[2] one mil thick film
[3] film thicknesses same as example 1
[4] film thicknesses same as example 5

An important property of an adhesive composite of the present invention is the capability to avoid accumulation of moisture under the composite when it is applied directly to skin. Moisture collection and retention properties of the adhesive composite were determined by applying composites to the backs of skin panel test participants who were then instructed to exercise until they began to perspire. The amount of moisture present on the skin was measured immediately after removal of the adhesive composite using an Evaporimeter (available from ServoMed, Sweden). Skin moisture was measured at 18, 22 and 33 hours after completion of exercise, with the results reported in g/sq. meter—24 hours as indicated in Table II below.

TABLE II

| | Time (hours) | | |
| --- | --- | --- | --- |
| Composite | 18 | 22 | 33 |
| Skin (no composite) | 173 | 322 | 317 |
| Example 1 | 386 | 397 | 406 |
| Tegaderm | 653 | 739 | 648 |

As may be seen from the above results, the moisture collection and retention properties of the dressings of the present invention are relatively close to uncovered skin. The adhesive composites of the present invention retain sufficient moisture to avoid desiccation of the wound site, but transmits sufficient moisture vapor to provide a beneficial healing environment.

What is claimed is:

1. An adhesive composite comprising
   a) a polymeric backing layer,
   b) a high moisture vapor transmission layer, and
   c) a skin contacting adhesive layer; wherein said high moisture vapor transmission layer is a polymeric film backing material that has a moisture vapor transmission rate of at least 2000 g/m²/24 hrs/37° C./100–20% RH when one mil thick as tested using the Upright Cup method and said high moisture vapor transmission layer is aqueous fluid and bacteria impermeable, and the polymeric backing layer is a polymeric film backing material having tensile strength when wet that is no more than 30% less than the tensile strength of the backing material when dry when one mil thick, provided that the material of layer a) is not the same as the material of layer b); and that the overall adhesive composite exhibits a moisture vapor transmission rate of at least about 1200 g/m²/24 hrs/37° C./100–20% RH.

2. The adhesive composite of claim 1 wherein the overall adhesive composite has a moisture vapor transmission rate that is greater than about 1500 g/m²/24 hrs/37° C./100–20% RH as tested using the Upright Cup method.

3. The adhesive composite of claim 1 wherein the overall adhesive composite has a moisture vapor transmission rate that is greater than about 2000 g/m²/24 hrs/37° C./100–20% RH as tested using the Upright Cup method.

4. The adhesive composite of claim 1 wherein the overall adhesive composite has a moisture vapor transmission rate that is greater than about 2500 g/m²/24 hrs/37° C./100–20% RH as tested using the Upright Cup method.

5. The adhesive composite of claim 1 wherein the polymeric backing layer is between about ⅓ to 1/20th of the thickness of said high moisture transmission layer.

6. The adhesive composite of claim 1 wherein said polymeric backing layer is less than about 0.025 mm thick.

7. The adhesive composite of claim 6 wherein said polymeric backing layer is less than about 0.020 mm thick.

8. The adhesive composite of claim 1 wherein said skin contacting adhesive layer is pattern coated.

9. The adhesive composite of claim 1 wherein said high moisture vapor transmission layer is selected from a polymeric film backing material that comprises polyether block amides.

10. The adhesive composite of claim 9 wherein said polymeric backing layer is a polyurethane film.

11. The adhesive composite of claim 1, wherein the high moisture vapor transmission layer absorbs between 10 and 100% of its own weight in water.

* * * * *

UNITED STATES PATENT AND TRADEMARK OFFICE
CERTIFICATE OF CORRECTION

PATENT NO. : 6,103,369
DATED : August 15, 2000
INVENTOR(S) : Lucast, Donald H.

It is certified that error appears in the above-identified patent and that said Letters Patent is hereby corrected as shown below:

Column 14,
Line 21, following "RH" and before "." insert -- using the Upright Cuff Method --.
Line 37, following "moisture" and before "transmission" insert -- vapor --.

Signed and Sealed this

Thirteenth Day of August, 2002

Attest:

JAMES E. ROGAN
Attesting Officer   Director of the United States Patent and Trademark Office